(12) United States Patent
Steward, Jr. et al.

(10) Patent No.: US 7,959,354 B2
(45) Date of Patent: Jun. 14, 2011

(54) ADJUSTABLE DENTAL X-RAY IMAGE MEDIA HOLDER

(75) Inventors: Curtis L. Steward, Jr., Sandwich, IL (US); Paul McDonough, Woodstock, IL (US); Thaddeus J. Hartlaub, Cherry Valley, IL (US); Nicole Sullivan, Elign, IL (US); Beverly M. Kunz, Huntley, IL (US)

(73) Assignee: Dentsply International, Inc., York, PA (US)

( * ) Notice: Subject to any disclaimer, the term of this patent is extended or adjusted under 35 U.S.C. 154(b) by 0 days.

(21) Appl. No.: 11/980,836

(22) Filed: Oct. 31, 2007

(65) Prior Publication Data

US 2010/0177875 A1  Jul. 15, 2010

Related U.S. Application Data

(63) Continuation-in-part of application No. 11/807,413, filed on May 29, 2007, now abandoned.

(51) Int. Cl.
*A61B 6/12* (2006.01)

(52) U.S. Cl. ......................................... 378/170; 378/168

(58) Field of Classification Search .................. 378/167, 378/168, 170, 181, 182, 183, 184
See application file for complete search history.

(56) References Cited

U.S. PATENT DOCUMENTS

| | | |
|---|---|---|
| 3,473,026 A | 10/1969 | Undergrove |
| 4,554,676 A | 11/1985 | Maldonado et al. |
| 4,866,750 A | 9/1989 | Chavarria et al. |
| 4,941,164 A | 7/1990 | Schuller et al. |
| 5,090,047 A | 2/1992 | Angotti et al. |
| 5,119,410 A | 6/1992 | Donato |
| 5,256,982 A | 10/1993 | Willis |
| 5,289,522 A | 2/1994 | Kanbar et al. |
| 5,327,477 A | 7/1994 | Levy |
| 5,513,240 A | 4/1996 | Hausmann et al. |
| 5,625,666 A | 4/1997 | Willis |
| 5,629,972 A | 5/1997 | Hausmann et al. |
| 6,461,038 B2 | 10/2002 | Pellegrine et al. |
| 6,652,141 B1 | 11/2003 | Cianciosi |
| 6,905,244 B2 | 6/2005 | Kilcher et al. |
| 7,033,075 B2 | 4/2006 | Landis et al. |
| 2004/0015176 A1 | 1/2004 | Cosman |
| 2004/0170253 A1 | 9/2004 | Landis et al. |
| 2004/0213382 A1 | 10/2004 | Andell et al. |
| 2005/0047550 A1 * | 3/2005 | Yao et al. ...................... 378/170 |
| 2005/0185767 A1 | 8/2005 | Puente et al. |
| 2005/0220272 A1 | 10/2005 | Glazer |

FOREIGN PATENT DOCUMENTS

| | | |
|---|---|---|
| EP | 0 379 611 | 8/1990 |
| EP | 0 397 599 | 3/1994 |
| WO | 83/01564 | 5/1983 |

* cited by examiner

*Primary Examiner* — Hoon Song
(74) *Attorney, Agent, or Firm* — Douglas J. Hura; Leana Levin; David A. Zdurne

(57) ABSTRACT

A dental x-ray image media holder (10) includes an image media backing plate (11) adjustably affixed to a bite block (12). The backing plate (11) has at least one channel (31-33) for receiving a post (21) affixed to the bite block (12), such that the bite block (12) can be selectively moved within the channel (31-33) to orient the bite block (12) in a predetermined position relative to the backing plate (11).

20 Claims, 17 Drawing Sheets

ADJUSTABLE DENTAL X-RAY IMAGE MEDIA HOLDER

TECHNICAL FIELD

The present invention is related to dental x-ray image media holders. More particularly the invention relates to a device for securing a dental x-ray image media including film, phosphor plates, digital sensors and the like, and holding it in place relative to the x-ray target during the x-ray procedure. Specifically the invention relates to a holder that can be selectively used to take a plurality of different x-rays using a plurality of different sizes, shapes or configurations of image media. The inventive device has a bite block moveably affixed to an image media backing plate. The backing plate may be provided with flexible straps to secure an image media to the backing plate.

BACKGROUND OF THE INVENTION

Dental professionals have employed x-ray imaging for many years. A traditional dental x-ray procedure includes exposing an x-ray film to x-ray energy after it has passed through the target site. The film is developed and an image of the target site is achieved. It has also long been known that in order to obtain a useful image, the dental x-ray film must be positioned relative to the target site in a predetermined and secure manner. Many numbers of x-ray film holders and positioning devices have been developed, including for example, that shown in U.S. Pat. No. 3,473,026 which is hereby incorporated by reference for background purposes.

More recently, many dental professionals have used digital x-ray sensors in place of traditional x-ray films. An example of such a sensor is shown for example in U.S. Pat. No. 6,652,141 which is hereby incorporated by reference for background disclosure of x-ray sensors. As with x-ray films, it is necessary for the x-ray sensor to be secured in a predetermined position during the x-ray imaging procedure. In a manner similar to the use of x-ray films, holding and positioning devices have been developed for x-ray sensors. Digital sensors often have attached electrical connection cords such that the digital sensor transfers data to a storage or display device such as a computer.

Another type of image media common in the dental industry is a phosphor imaging plate. The x-ray shot is stored onto the imaging plate which is later read by a scanning machine or the like and the data is transferred to a storage or display device, such as a computer.

These and other type of devices that receive dental x-rays for dental purposes are herein collectively referred to as dental x-ray imaging media, sensors, imagers or the like. Any such devices that are sensitive to such x-rays is within the scope of the invention. It will be appreciated from the above discussion that the different image media holders while all accomplishing similar purposes, that is, dental diagnostics and the like, all operate in different manners. It is also the fact that the image media themselves are different in shape, size and configuration. For example, traditional x-ray films are often manufactured inside an envelope before being used with a patient. Phosphor imaging plates are often very thin, not much thicker than a sheet of paper or two and are placed into a barrier envelope before being used in an x-ray procedure. Digital sensors tend to be fairly thick in respective comparison due to the internal energy sensing components required for such devices. It is envisioned that in the future, other type of dental imaging media will be developed using similar or perhaps completely different technologies. These all have at least some commonality in that they generally must fit within the oral cavity and they must be securely held in a desired location during the x-ray procedure.

Adding to the complexity of using different imaging media is that even within a common type of media different manufacturers often provide media products that while they accomplish the same task as other media, are of a different size, shape or configuration.

Of course, it is also known that different set-ups must often be used for taking an x-ray image of different parts of the oral cavity. For example, conventionally dental x-rays taken in the oral cavity include anterior vertical periapical, anterior horizontal periapical, posterior horizontal periapical, posterior vertical periapical, horizontal bite-wing, vertical bite-wing, left and right images and other similar x-ray positions.

It will be appreciated that given the large number of different imaging media of different sizes, shapes and configurations, and given that many different x-ray procedures may be required in the oral cavity which require varied positioning of the imaging media relative to the tooth or other target site, the imaging media holder will have a different configuration for each possible combination. This requires the dental practitioner to normally stock a large number of imaging media holders in order to be reasonably certain that a proper holder is available at any given time for an x-ray procedure. It takes time and effort to match holders to specific imaging media.

A need exists therefore for a universal dental x-ray imaging media holder that will securely affix different shapes, sizes and configurations of such imaging media. It would also be desirable if the same holder could be used to hold such different media in a selected location during an x-ray procedure and which can be used to take more than one type of x-ray by being positioned at different locations in the oral cavity. The present invention provides an adjustable holder that meets these desires.

SUMMARY OF THE INVENTION

In general, a dental x-ray image media holder comprises an image media backing plate adjustably affixed to a bite block. The backing plate has at least one and preferably a plurality of channels for receiving a post affixed to the bite block, such that the bite block can be selectively moved within the channels to orient the bite block in a predetermined position relative to the backing plate. The invention is carried out by the invention as hereinafter described and claimed.

PREFERRED EMBODIMENTS FOR CARRYING OUT THE INVENTION

Figure 1:
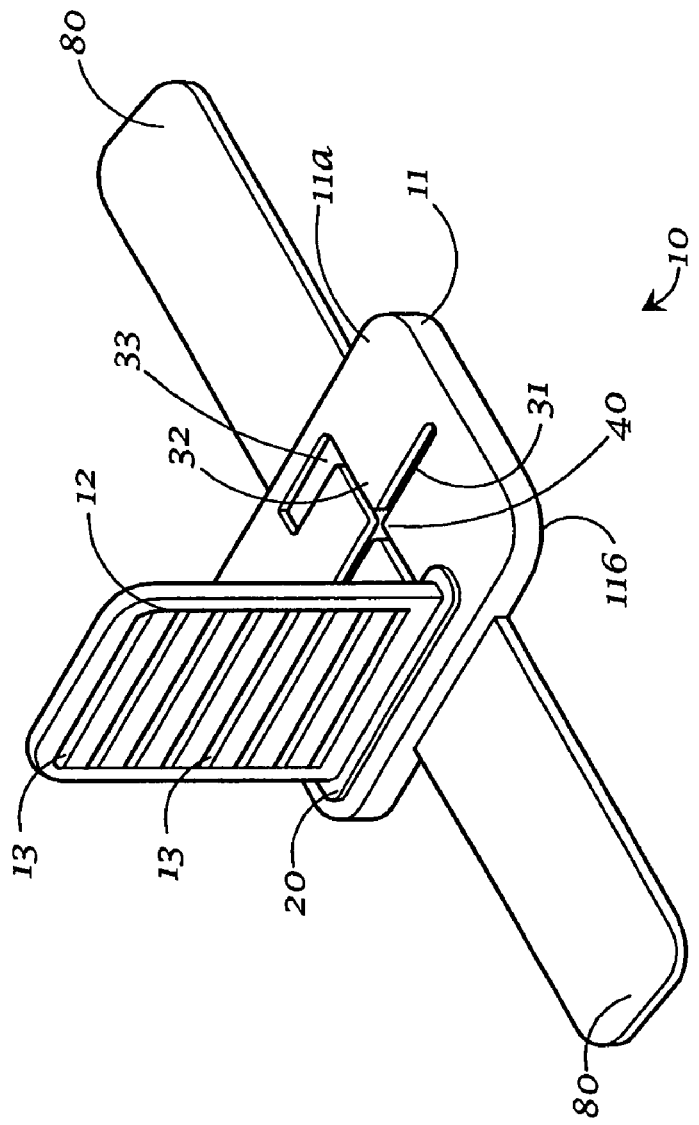
FIG. 1 is a perspective view of a dental image media holder embodying the concepts of the present invention.
Figure 2:
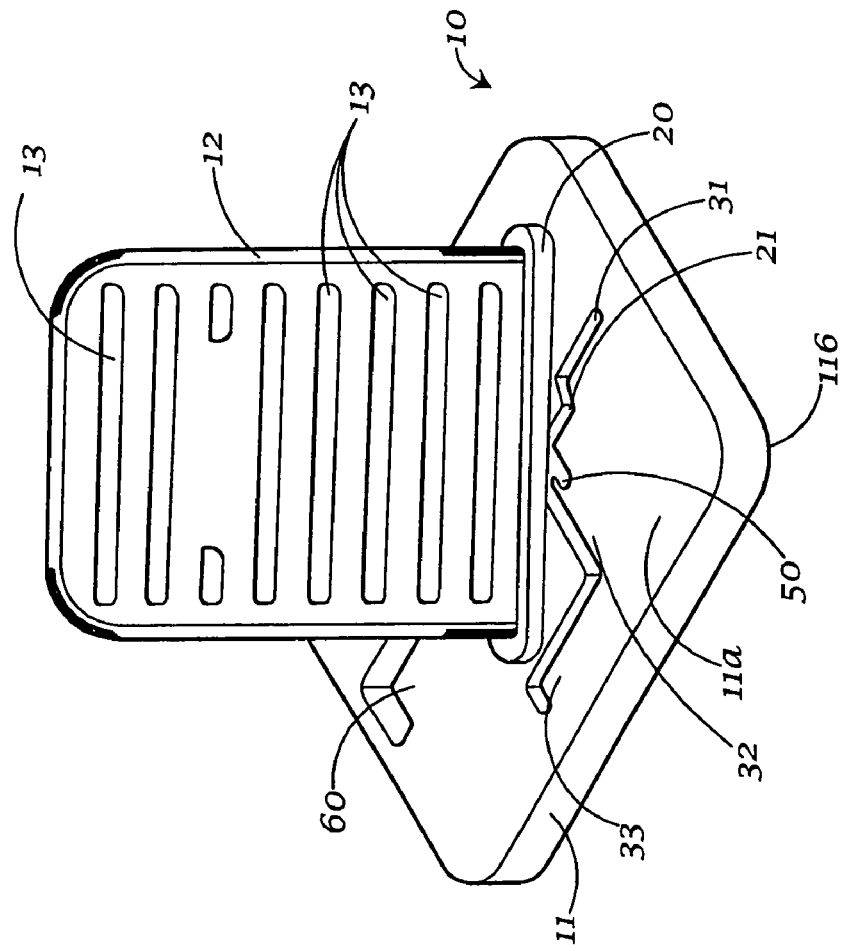
FIG. 2 is a perspective view of a portion of the image media holder of FIG. 1, showing a bite block in a position where adjustment thereof relative to a backing plate can take place.
Figure 3:
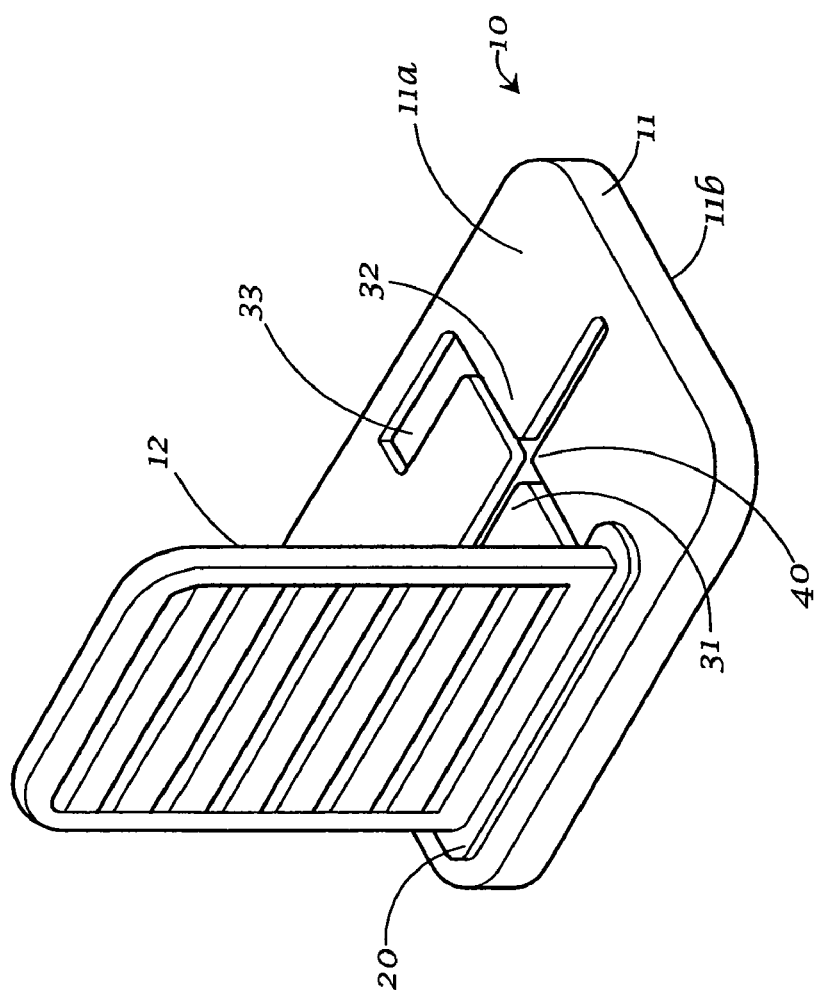
FIG. 3 shows the image media holder of FIG. 2 with the bite block in still another position.

An image media holder embodying the concepts of the present invention is generally designated on the attached drawings by the number 10. Image media holder 10 has a backing plate 11 configured to have a first side 11a and a second side 11b. While backing plate 11 may be of any size or shape, it has been found that a generally rectangular and flat plate is conducive to physically contacting and supporting a dental x-ray image media in a manner to be hereinafter described. Of course, any size, shape or configuration is within the scope of the invention although it will be exemplified and is preferred to be of the flat plate design as shown on the drawings.

Image media holder 11 is also provided with a bite block 12. It will be understood by those skilled in the art that a "bite block" used with a dental x-ray image media holder is intended to be physically impinged between the teeth, gums or other patient dentition during x-ray procedures. As is convention, the image media holder will be positioned in a patient's oral cavity (not shown) and the patient will be instructed to bite upon the block. This locates the affixed or supported x-ray image media during the ensuing procedure. Bite block 12 of the invention is of any suitable and conventional design, shape or configuration except for the unique inventive aspects to be described hereinbelow.

One preferred bite block 12 is generally flat and rectangular, and may be provided with gripping ridges 13 as is conventional. Also preferably, bite block 12 may be provided with a baseplate 20 at one end thereof, preferably at one of the shorter ends of its rectangular body if a rectangular design is chosen. Baseplate 20 is configured to be generally smooth such that intimate physical contact between it and first side 11a of backing plate 11 can be made. Still more preferred, that physical contact is such that baseplate 20 can slide across the surface of first side 11a of backing plate 11 for purposes that will become clear from the following discussion.

Figure 12:
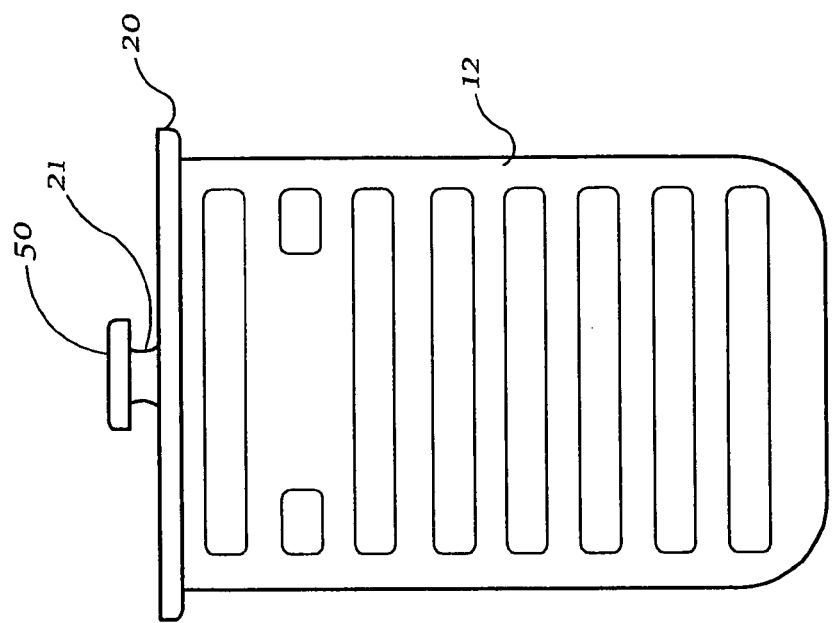
FIG. 12 is a front elevational view of the bite block component of the holder of FIG. 1.

Extending from bite block 12 and more preferably from baseplate 20, is a positioning post 21 (FIG. 12) that will cooperatively interact with backing plate 11 in a manner to now be described.

In order to allow bite block 11 to be positioned in more than one position relative to backing plate 20, there is preferably provided in backing plate 11 at least one and preferably a plurality of slots or channels 31-33. Channels 31-33 may be of any design or configuration and may extend completely through backing plate 11 from first side 11a to second side 11b. Alternatively, channels 31-33 may extend only partially through from first side 11a and not all the way to second side 11b.

Post 21 affixed to bite block 12 is configured such that it can be received within channels 31-33. By sliding within a selected one of channels 31-33 to any preselected position therein, it will be appreciated that bite block 12 can be so positioned wherever it is desired. To allow positioning of bite block 12 relative to backing plate 11 and to accommodate at least the taking of dental x-rays to include anterior vertical periapical, anterior horizontal periapical, posterior horizontal periapical, posterior vertical periapical, horizontal bite-wing, vertical bite-wing or others, it is preferred to have a primary channel 31, a secondary channel 32, and a first and second tertiary channels 33, although of course, any number of channels of any design, shape or intersection is within the scope of the invention.

In one embodiment of the invention, channels 31-33 are substantially linear although any shape is within the scope of the invention. In this embodiment, primary channel 31 may intersect secondary channel 32 at some midpoint of the respective channels. By midpoint it is simply meant at some point between their respective ends. In a preferred configuration, the intersection 40 of primary channel 31 and secondary channel 32 is at the approximate center of secondary channel 32 and somewhat removed from the center of primary channel 31 such that the two from a "t". Tertiary channels 33 may intersect any other channels, but for the sake of the drawings a preferred embodiment is shown where each tertiary channel 33 at one of its own ends intersects an end of secondary channel 32.

As stated above, the exact design, dimensions or other characteristics of channels 31-33 can be varied but they should be such that they can receive and guide post 21 and hence, bite block 12. It will be appreciated that by sliding bite block 12 over the surface of backing plate 11, such sliding being guided by the physical contact of post 21 within a selected channel 31-33, bite block 12 can be positioned relative to backing plate 11 in any desired location. It will be further appreciated that bite block 12 can be moved from one channel such as primary channel 31 to another channel such as secondary channel 32 by moving post 21 (and hence the attached bite block 12) within the channel to the intersection thereof such as intersection 40 and thereby continue to move the post 21 to the other channel. Post 21 thus moves within a channel 31-33 in a sliding manner.

It is also preferred to provide a base 50 at an end of post 21 and provide channels 31-33 that completely pass through backing plate 11 between its two sides 11a and 11b, such that channels 31-33 are open slots. Post 21 thereby extends between and connects bite block 12 or baseplate 20 if employed, and base 50. By configuring base 50 to be wider than channels 31-33, and by configuring post 21 to be of suitable dimension, backing plate 11 can be caused to be physically received between base 50 and bite block 12. This physically affixes bite block 12 to backing plate 11 in an otherwise adjustable manner by use of the channels 31-33 as already described. Again it will be appreciated that bite block 12 while being held to backing plate 11 is free to be positioned anywhere within channels 31-33 and may even be rotated on an axis or rotation provided by post 21, thereby accommodating any or all of the numerous x-ray positions required by a dental practitioner. In a preferred embodiment, the bite block 12 is rotated on post 21 with post 21 acting as an axle or rather its axis acts as an axis of rotation. In a further embodiment, post 21 and channels 31-33 are configured and dimensioned in shape or size such that bite block 12 can be rotated only at an intersection of at least two channels 31-33, although this is not necessarily required.

A larger opening or expanded area 60 may be provided in one or more channels, of such size as to pass base 50 to aid assembly of the image media holder 10 component parts. Expanded area may also provide an area where post 21 can be more easily rotated therein.

In a preferred embodiment of the invention, image media holder 10 is fabricated from any suitable material usable in the oral cavity. More preferred image media holder 10 is fabricated from a plastic material and the image media holder 10 is disposable.

There is also provided according to the invention some means of securing or affixing, preferably in a removable manner, an image media such as imaging plate 70 and digital sensor 71 to the second side 11b or backing plate 11. Two preferred methods include a releasable or pressure-sensitive adhesive (not shown) and straps 80, which may be used separately or in combination with each other.

Figure 4:
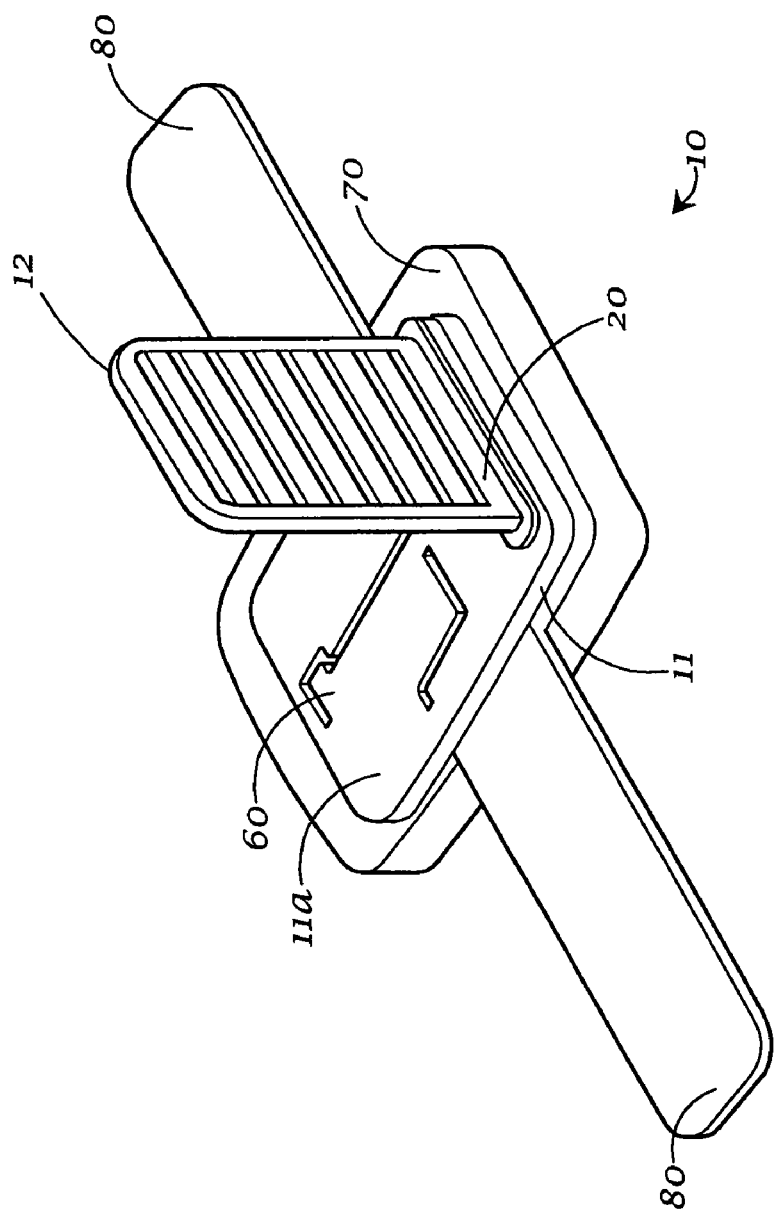
FIG. 4 Fig. is a perspective view of a the image media holder as in FIG. 1, showing a bite block adjusted to a different position.

Any adhesive suitable for use in the oral cavity is within the scope of the invention, and the specific adhesive chosen is not necessarily a limitation of the invention. One preferred adhesive is a latex-free, pressure-sensitive adhesive which is coated onto second side 11b or backing plate 11 in any conventional manner. A release strip (not shown) may be employed to cover the adhesive until used. As shown for example, in FIG. 4, an image media such as plate 70 can be physically pressed onto second side 11b of backing plate 11 and held in place by the pressure-sensitive or other adhesive employed.

Figure 7:
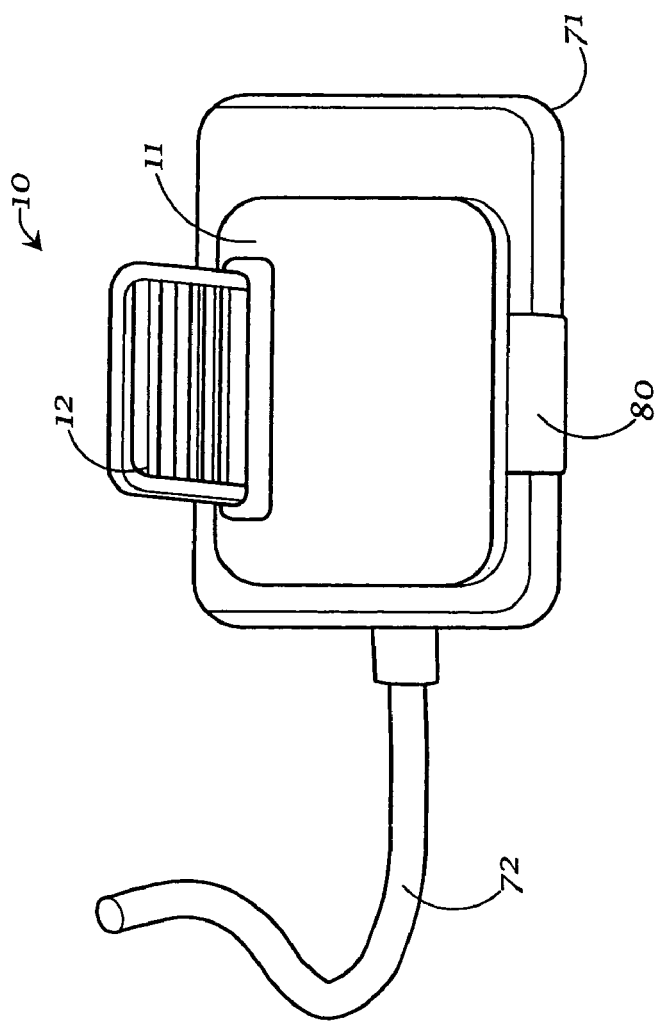
FIG. 7 is a top perspective view of the image media holder of FIG. 6, showing a means of affixing an image media to the image media holder.
Figure 8:
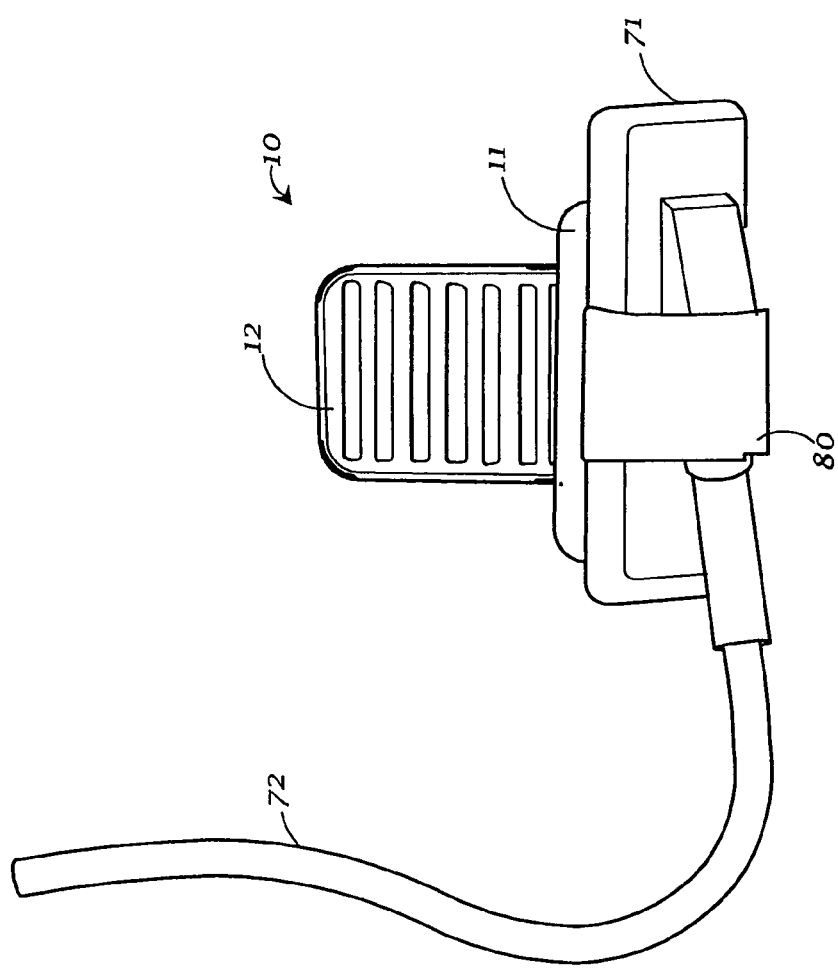
FIG. 8 is a bottom perspective view of the image media holder of FIG. 7.

If a strap 80 is employed and two are preferred, it is affixed to backing plate 11 and is preferably flexible in one direction yet rigid in another. Once the image media such as plate 70 is caused to physically contact backing plate 11, strap 80 (or straps 80 if more than one are used) is wrapped around plate 70 (or any other imaging media as may be employed) in a manner allowed by the flexibility of strap 80, to thereby hold the imaging media to backing plate 11 (FIGS. 7 and 8). Straps 80 may also be provided with a suitable adhesive or they may be provided with any other conventional means to affix them in the securing position. By all such manner or combinations thereof, straps 80 and/or the adhesive positively secure and otherwise affix (preferably in a removable manner) an imaging media to holder 10.

Figure 5:
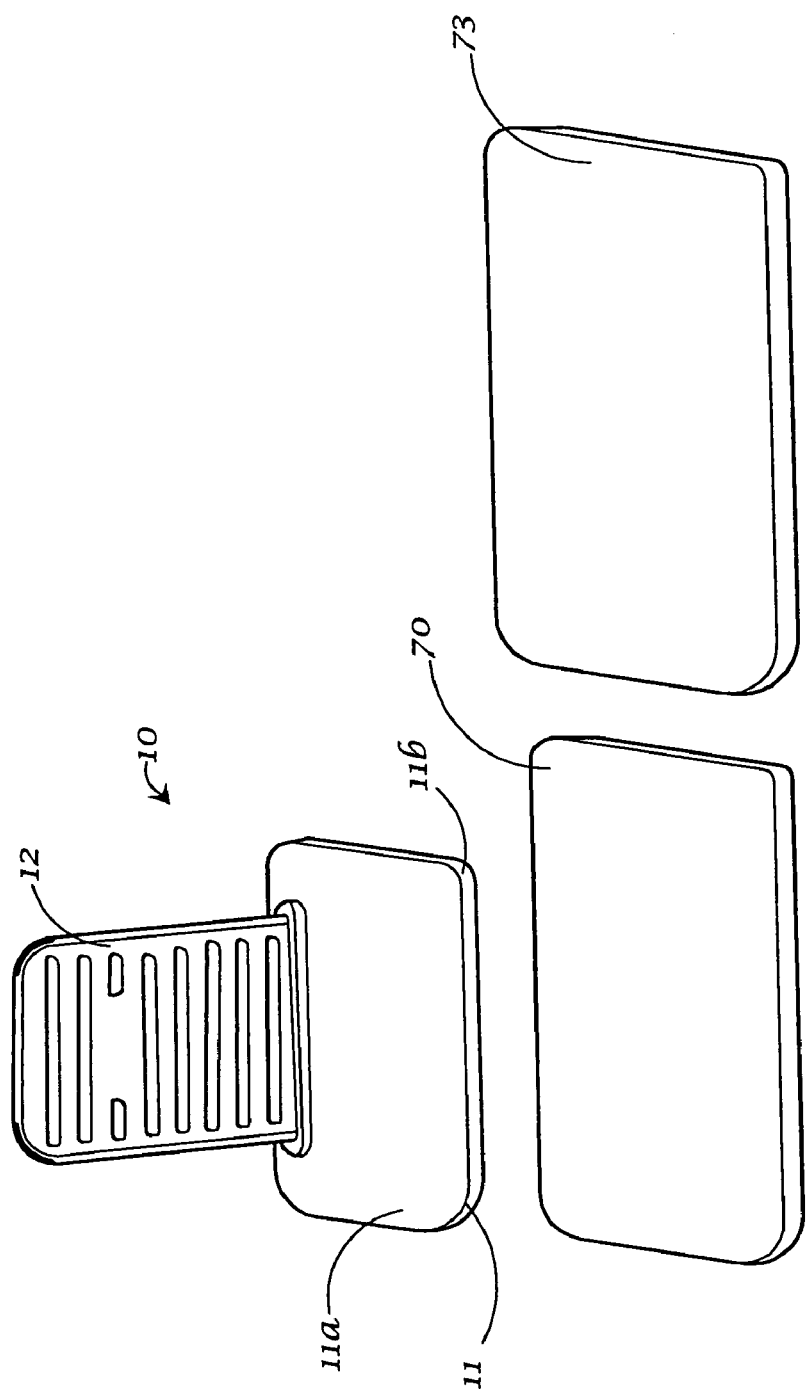
FIG. 5 is a partially exploded view of an image media holder as in FIG. 2 shown for environmental purposes in conjunction with a phosphor imaging plate and a barrier envelope for the phosphor plate.
Figure 6:
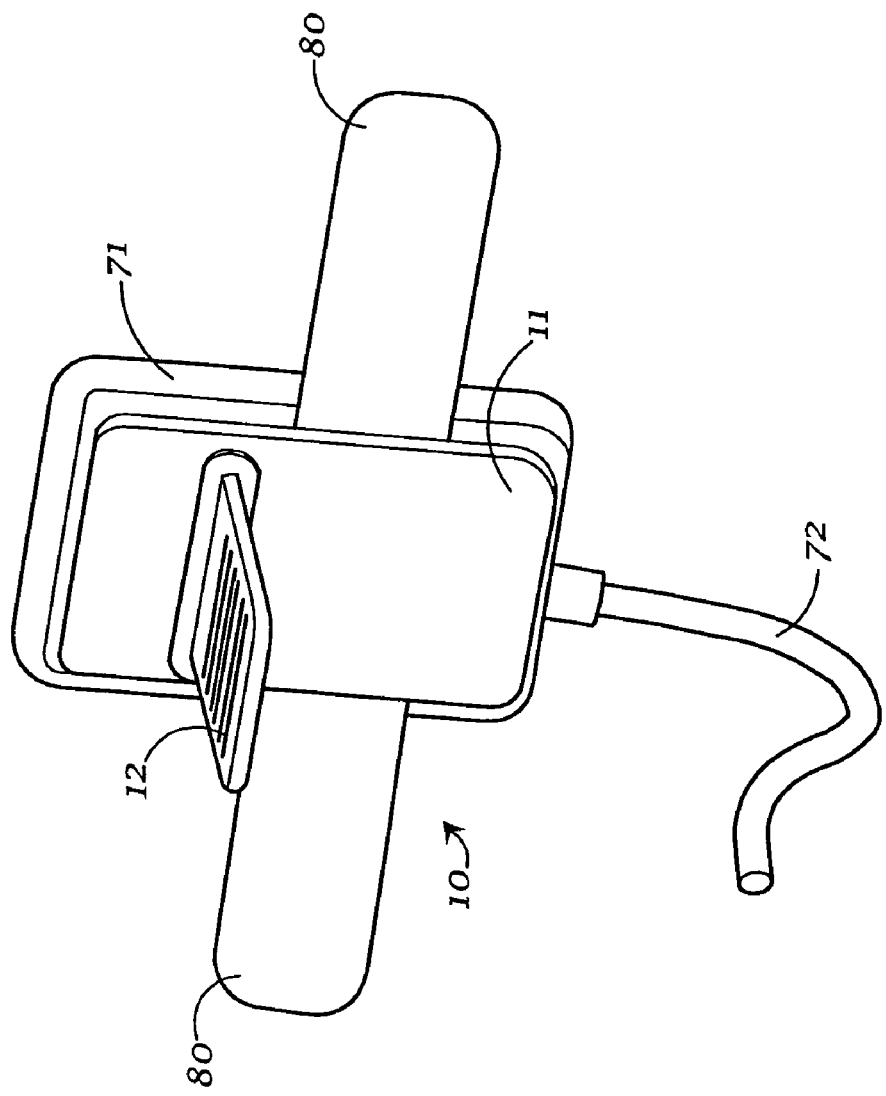
FIG. 6 is a top perspective view of an image media holder as in claim 1, shown for environmental purposes holding a digital dental sensor having an attached cord (partially shown).
Figure 9:
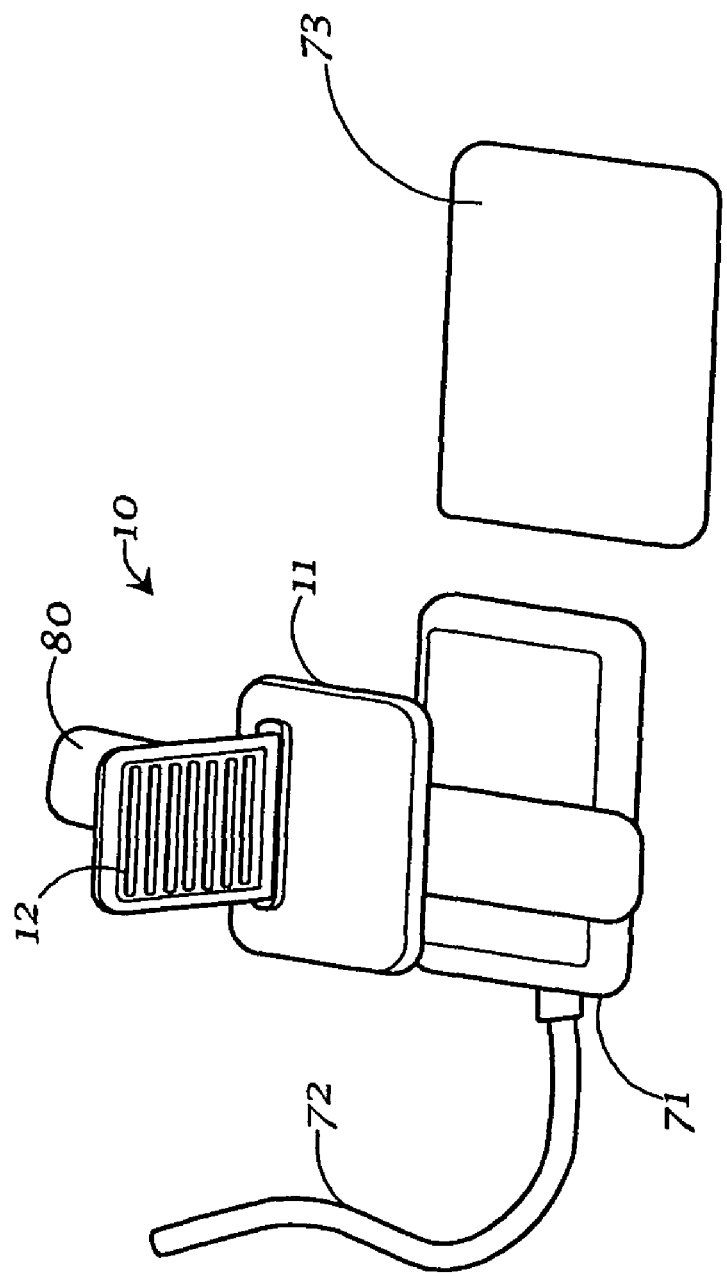
FIG. 9 is a partially exploded view of the image media holder of FIG. 6, showing for further environmental purposes a cover sleeve for the image media.

It will be appreciated that by suitably designing straps 80, any of a large number of image media designs such as for example, plate 70 or digital sensor 71 can be held by image media holder 10. Just as a belt may be adjusted to secure items of different size or shape, strap 80 may also accommodate different imaging media due to the length or other dimensions of strap 80. The design can accommodate different image media such as plate 70, relatively thicker image media such as digital sensor 71, and even other items such as connecting wire 72 for digital sensor 71 or conventional protective sleeves or barriers 73 (FIGS. 5 and 9) for such image media. Although not depicted, a conventional dental x-ray film packet or indeed any other dental image media can be held by the inventive image media holder 10. It is even contemplated that the present invention can secure and hold such imaging media as may be developed in the future.

Figure 10:
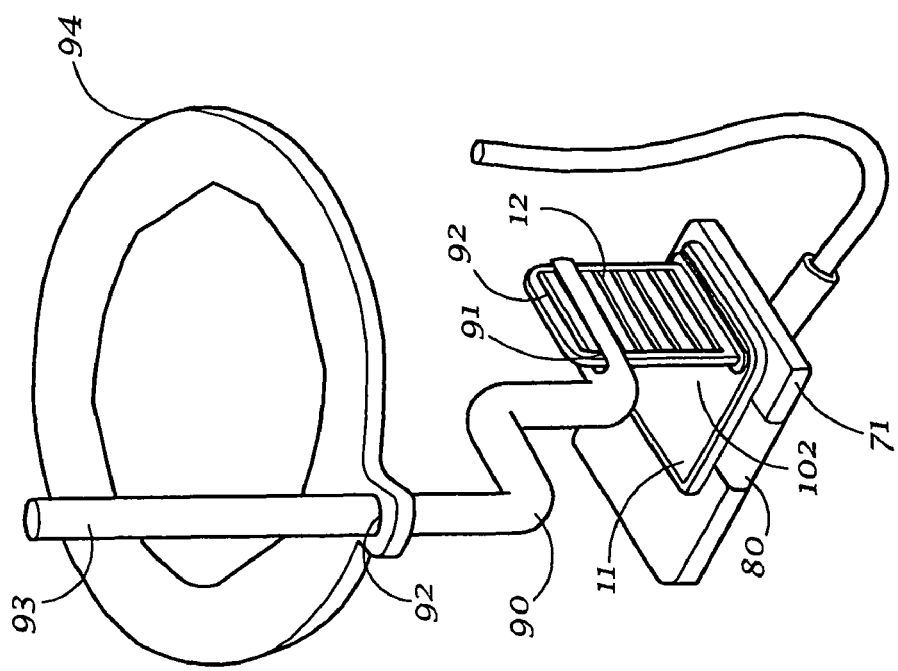
FIG. 10 is a perspective view of an alternative embodiment of an imaging media holder according to the present invention, and shown with an attached arm and aiming ring.
Figure 11:
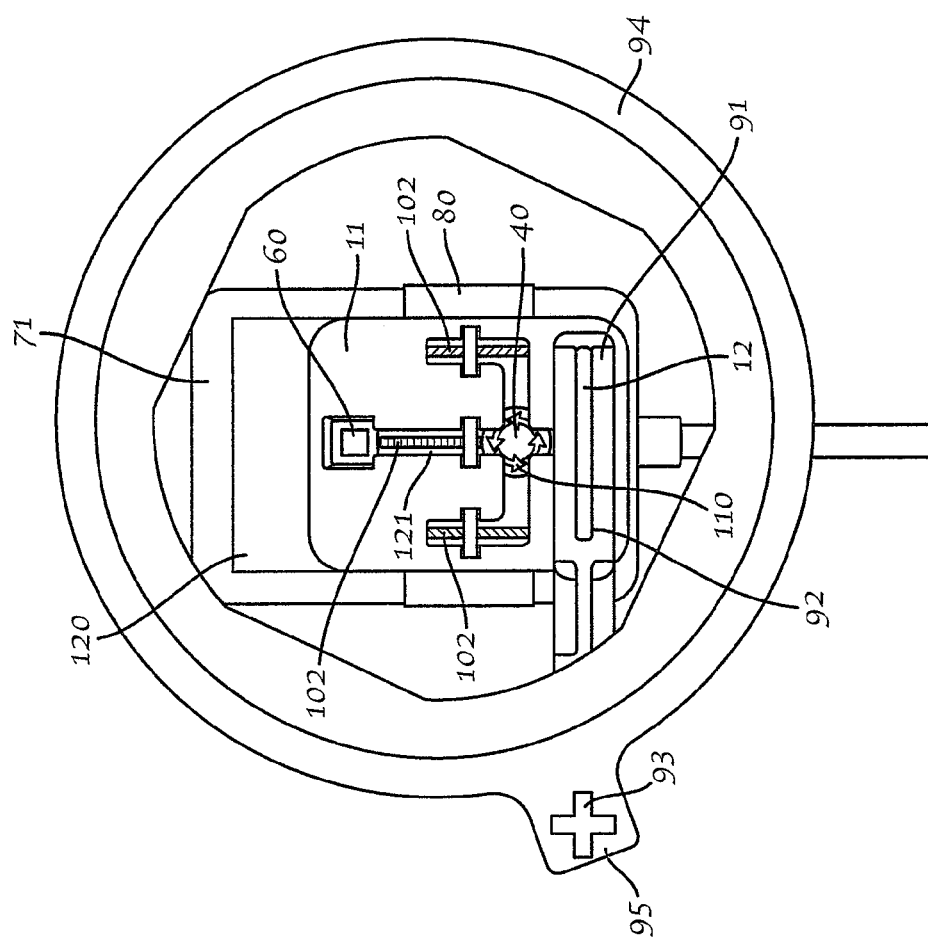
FIG. 11 is a top plan view of the holder of FIG. 10.

It is known in the dental x-ray art to provide aiming rings mounted upon arms or other structures to in turn, effectively connect the aiming ring to an imaging media holder. The present invention can be so configured as is shown in FIGS. 10 and 11. Any means of affixing an arm and aiming ring to holder 10 is within the scope of the invention. One preferred means is to provide an arm 90 having a fixing member 91 provided with a slot 92. Slot 92 is configured and sized to physically receive and frictionally hold an edge of bite block 12 therein. At location distal to fixing member 91 is a support post 93 which is configured to receive or otherwise adjustably secure an aiming ring 94 thereto. For example, post 93 may have a certain shape such as the cross-shape depicted in the drawings and a complementary shaped aperture 95 may be provided at some location in aiming ring 94, such that post 93 is placed through aperture 95 in use. Aiming ring 94 is free to slide along post 93 to any desired position and is frictionally held in place by its physical contact with post 93.

In an alternative embodiment of the invention (FIGS. 10 and 11), a backing plate 11 is provided with indicia 102 which separately indicate a different position for a specific x-ray procedure. Indicia 102 may be colors, numbers, letters, symbols, protrusions, detents, striations, or any other physical or visual indicators without limitation, or even combinations thereof. For example, backing plate 11 may be provided with more than one distinct indicia 102, which might indicate for example, by different colors the position to which bite block 12 should be moved to take a left bitewing or a right bitewing respectively. Further still, if holder 10 is of the type wherein bite block 100 can be rotated on post 21 as an axis of rotation and only at a certain point such as the intersection of certain channels 31-33, further indicia such as arrows 110 may be provided at the intersection or other area where such rotation is permitted.

Indicia 102 and 110 may be provided on a separate layer of material, such as a plastic sheet 120 which can be positioned in a juxtaposed physically contacting relationship with second side 11b of backing plate 11. In a preferred embodiment, straps 80 and integrally formed with and from the same material as sheet 120. In this configuration, it may be advantageous to provide a backing plate 11 which is at least partially transparent, such that indicia 102 placed upon sheet 120 may be viewed therethrough. While it will be appreciated that a transparent or at least partially transparent bite block 11 will facilitate viewing the indicia 102 or 110 therethrough when sheet 120 is employed, it is also possible to simply provide large enough openings 121 in bite block 100 so as to view indicia 102 or 110 therethrough. Further still, channels 31-33 may themselves be suitably positioned such that the indicia 102, 110 is viewable therethrough.

Figure 13:
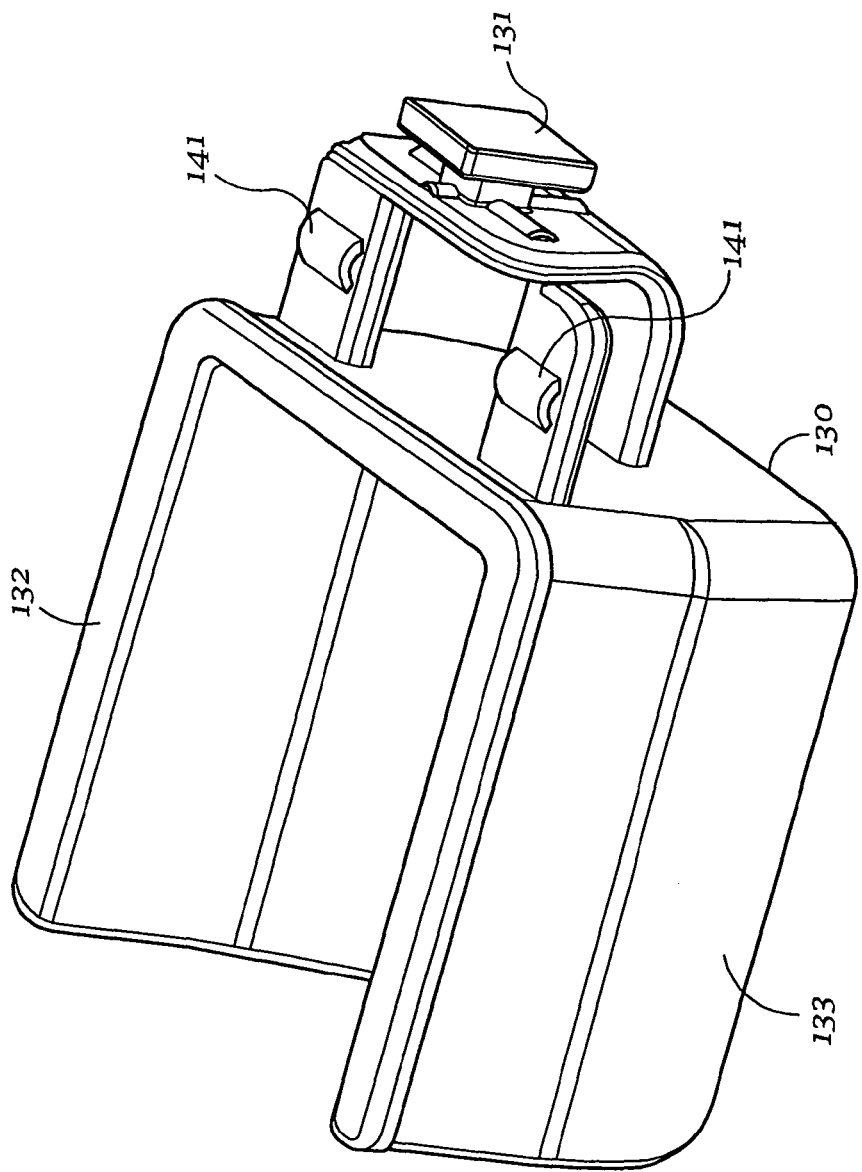
FIG. 13 is a perspective view of an alternative bite block useful with the present invention.
Figure 14:
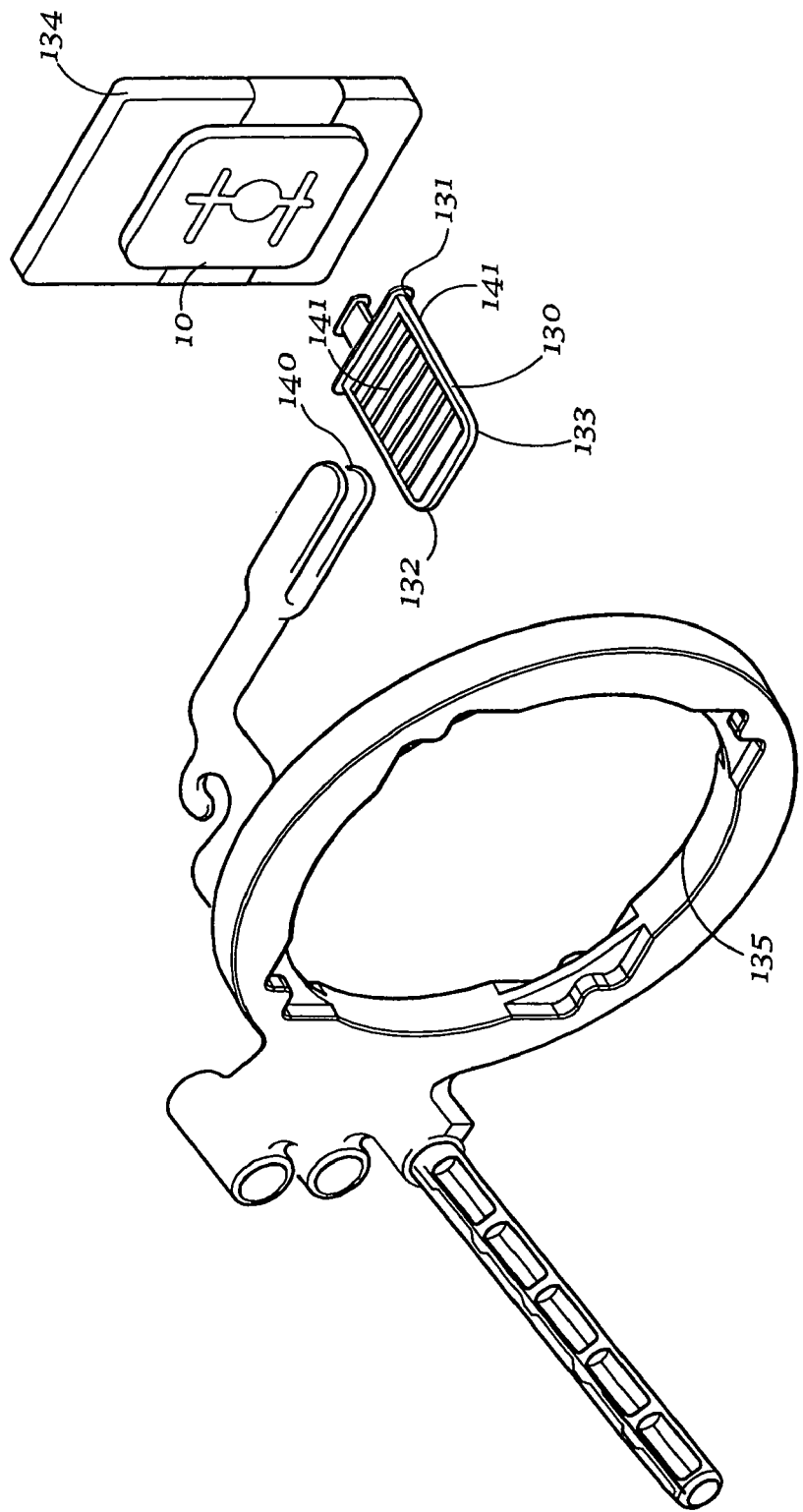
FIG. 14 is a perspective view of an exemplary aiming ring and image media receptor shown in an exploded view with the media holder and bite block of the invention.
Figure 15:
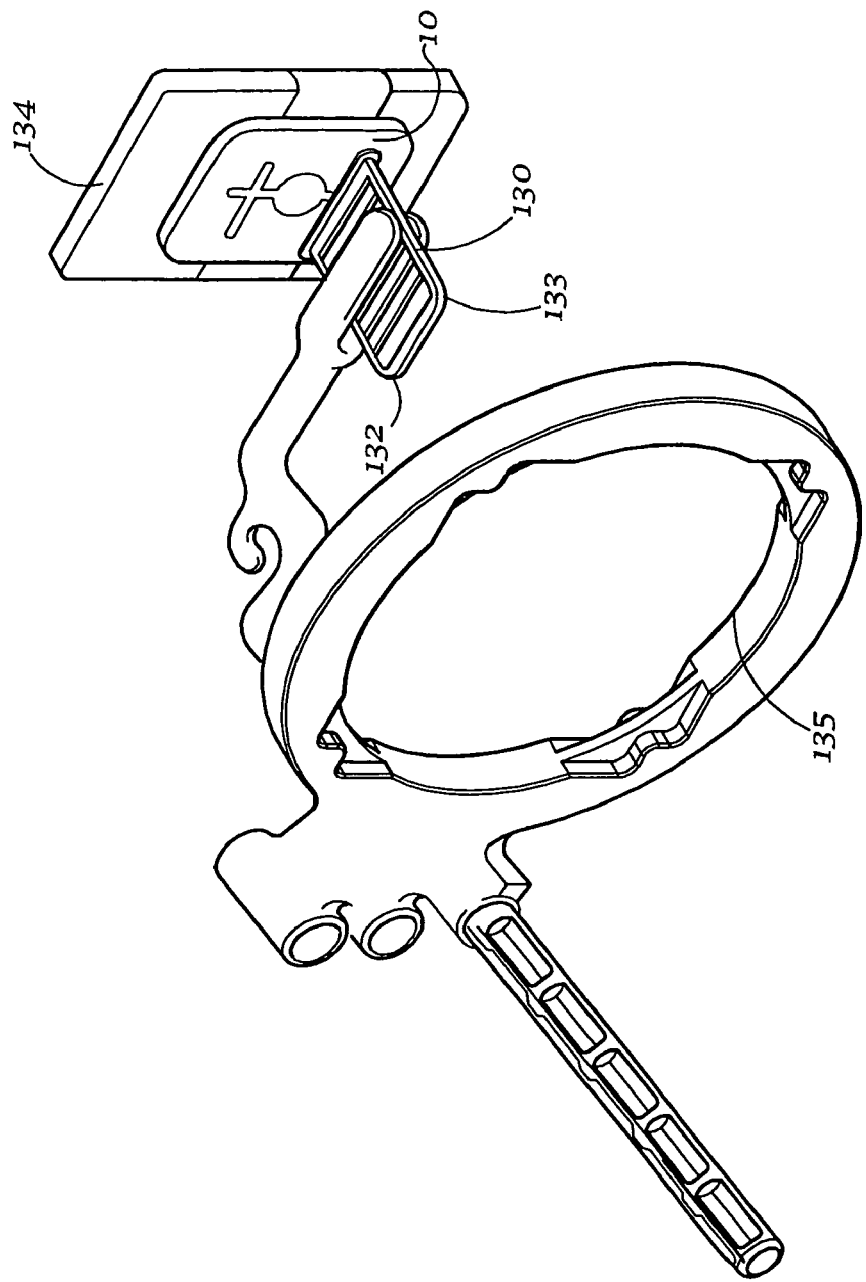
FIG. 15 is a perspective view as in FIG. 14 shown assembled.

An alternative embodiment of a bite block is designated by the number 130 on the attached drawings, namely, FIGS. 13-15. Bite block 130 is especially configured to be useful during endodontic or "root canal" procedures. As is known (but not shown) during the root canal procedure an endodontic file is used to remove the nerve from the tooth and cleanse the nerve tract within the root of the tooth. While the file is in place in the tooth, it is necessary to X-ray the tooth to assure that the endodontic file has been inserted deeply enough into the root of the tooth so that all of the nerve tract will be removed. This procedure must be done with the file in place and before it is removed.

Bite block 130 is provided with a base 131 for operative connection with inventive holder 10 in the manner described above, and is provided with a first and second bite arms 132 and 133. Arms 132 and 133 are preferably arranged in a spaced, parallel and opposing relation as shown on the drawings. By being spaced, there is room for an endodontic file to remain in place in the root canal during the taking of an x-ray image. It will be appreciated that base 131 allows positioning of a sensor such as exemplary sensor 134 in multiple positions in the same inventive manner as described hereinabove with respect to holder 10.

Further, it is preferred although not required that bite block 130 be provided with means for being affixed or removably affixed to an aiming ring 135. For example, ring 135 may be provided with spaced, opposing parallel grooves 140 and bite block 130 may be provided with complementary pins 141. Grooves 140 and pins 141 may be configured such that grooves 140 may be frictionally fit over pins 141 by sliding. The friction between grooves 140 and pins 141 may be sufficient to hold ring 135 in place as needed. It will be appreciated that any means of affixing bite block 130 to ring 135 is within the scope of the invention.

Figure 16:
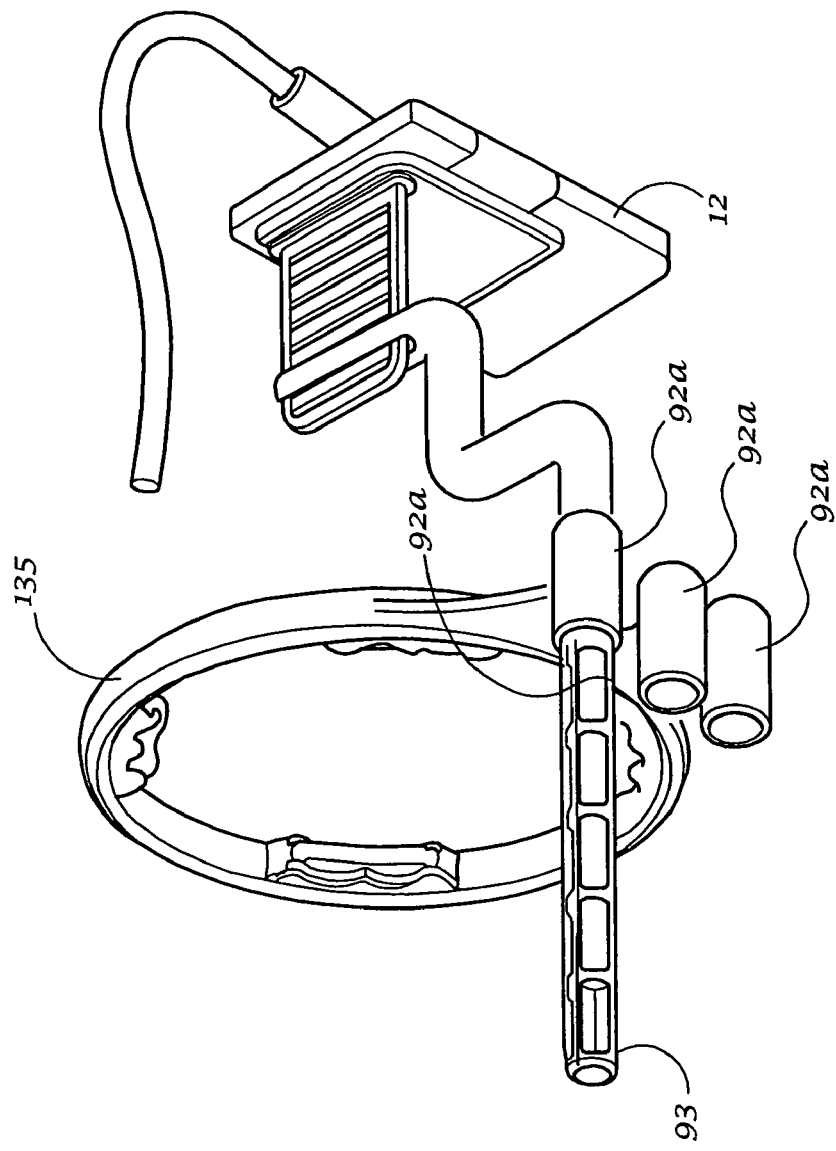
FIG. 16 is a perspective view of an alternative embodiment of the present invention, shown with an exemplary dental x-ray sensor for environmental purposes.
Figure 17:
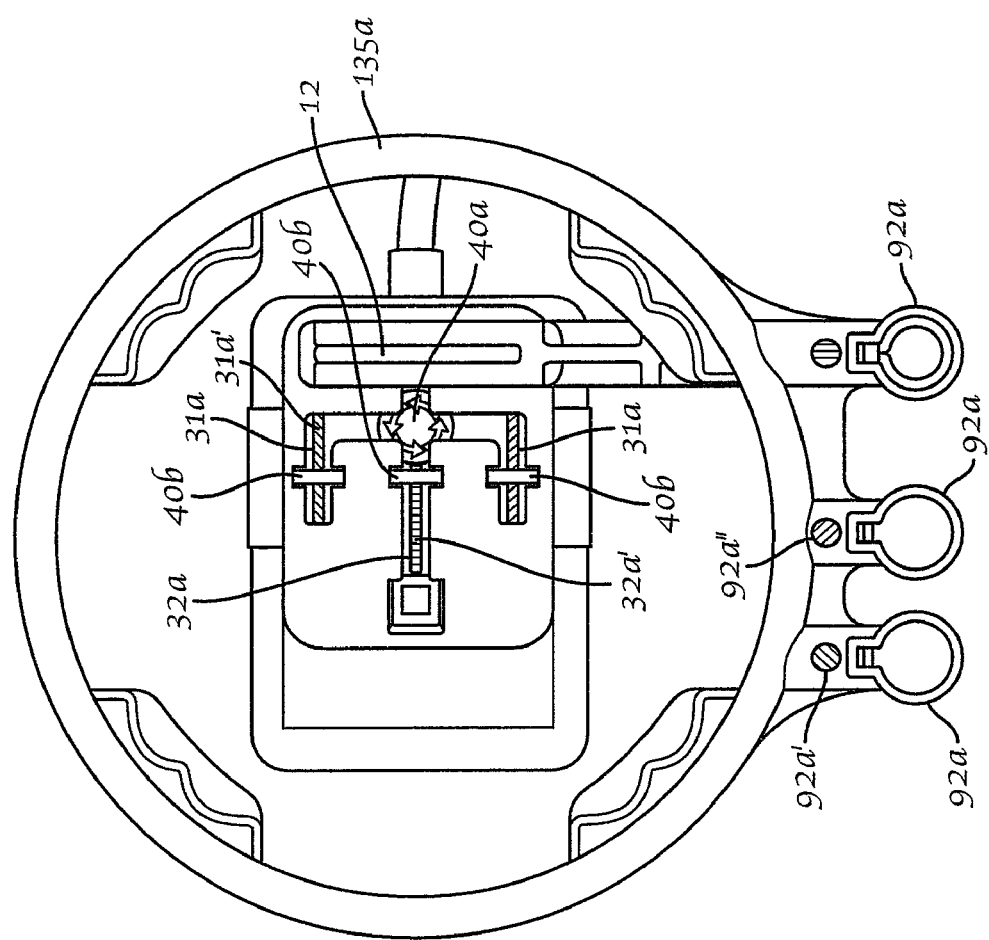
FIG. 17 is a side, plan view of the alternative embodiment shown in FIG. 16.

An alternative configuration of channels are shown as channels 31a and 32a, and an alternative intersection is shown as intersection 40a in drawings FIGS. 16 and 17. In addition, intermediate rotation permitting open areas 40b are provided at a variety of points such that bite block 12 may be rotated at a point away from intersection 40a, if desired. In addition, aiming ring 135a similar to aiming ring 135 may be provided with a plurality of supports 92a each capable of supporting arm 93. In a preferred configuration, each support 92a holds arm 93 in a preselected position facilitating the taking of a particular dental x-ray image. Further still, indicia 31a' and 32 a' within channels 31a and 32a respectively, and indicia 40a' in intersection 40a correspond to indicia located upon, adjacent or otherwise affiliated with a given support 92a. For example, indicia 31a' might be a color such as the color yellow, which corresponds to yellow color indicia 92a' positioned close too and hence affiliated with or otherwise indicating support 92a. When bite block 12 is positioned within channel 32a, as such was described above, the user will place arm 93 within support 92a knowing that the assembled elements are now in the proper position for a given x-ray imaging procedure. As a further example, indicia 31a' and associated support 92a indicated to the user by indicia 92a', might be useful for the taking of a posterior image. Indicia 32a' and associated support 92a" might be a second color such as red, and may indicate the proper position for the taking of a bitewing image. Other positions may be proper for the taking of an anterior image, and the like and for example, the setup depicted in FIG. 16 happens to be useful for the taking of an anterior x-ray image. Of course, any indicia such as colors, numbers, verbiage, marks, scribes, bumps, voids, physical structures or the like applied in any manner are within the scope of the invention.

It will be appreciated therefore, that an image media holder 10 as described is capable of holding image media of different designs, shapes and configuration. The inventive image media holder is also capable of allowing the user to take dental x-rays in more than one position. All of these different uses can be accomplished with one image media holder according to the invention. The preferred embodiments for carrying out the invention have been described herein and shown on the attached drawings without attempting to show all variations that fall within the scope thereof. Therefore, the scope of the invention will be determined only by the attached claims.

What is claimed is:

1. A dental x-ray image media holder comprising an image media backing plate adjustably affixed to a bite block; said backing plate having at least one channel for receiving a post affixed to said bite block, such that the bite block can be selectively moved within said channel to orient the bite block in a predetermined position relative to the backing plate; wherein the backing plate is provided with a plurality of indicia, such that at least one of said indicia is used to indicate the position of the bite block relative to the backing plate, which is associated with a predetermined dental imaging procedure; and wherein the backing plate is provided with at least two intersecting said channels.

2. The dental x-ray image media holder as in claim 1 further comprising an aiming ring adjustably secured to the holder with a support arm.

3. The dental x-ray image media holder as in claim 2 wherein said support arm is affixed to said bite block or removably affixed to said bite block.

4. The dental x-ray image media holder as in claim 3 wherein said support arm is provided with a slot for receiving said bite block, such that said bite block is frictionally retained therein.

5. A dental x-ray image media holder comprising an image media backing plate adjustably affixed to a bite block; said backing plate having at least one channel for receiving a post affixed to said bite block, such that the bite block can be selectively moved within said channel to orient the bite block in a predetermined position relative to the backing plate; wherein the backing plate is provided with a plurality of indicia, such that at least one of said indicia is used to indicate the position of the bite block relative to the backing plate, which is associated with a predetermined dental imaging procedure; and wherein said backing plate is provided with at least four said channels, at least two of which intersect at midpoints thereof.

6. The dental x-ray image media holder as in claim 5 wherein at least one of said four channels has a first and second end and intersects at least one other said channel at one of its said first or second ends.

7. The dental x-ray image media holder as in claim 6, wherein said channels include a t-shaped configuration made up of a primary channel intersecting a secondary channel at a midpoint of each said primary and secondary channels, and at least one tertiary channel having a first and second ends and intersecting at its first end with an end of said secondary channel.

8. The dental x-ray image media holder as in claim 5 further comprising an aiming ring adjustably secured to the holder with a support arm.

9. The dental x-ray image media holder as in claim 8 wherein said support arm is affixed to said bite block or removably affixed to said bite block.

10. The dental x-ray image media holder as in claim 9 wherein said support arm is provided with a slot for receiving said bite block, such that said bite block is frictionally retained therein.

11. A dental x-ray image media holder comprising an image media backing plate adjustably affixed to a bite block; said backing plate having at least one channel for receiving a post affixed to said bite block, such that the bite block can be selectively moved within said channel to orient the bite block in a predetermined position relative to the backing plate; wherein the backing plate is provided with a plurality of indicia, such that at least one of said indicia is used to indicate the position of the bite block relative to the backing plate, which is associated with a predetermined dental imaging procedure; and wherein at least one of said channels is provided with an expanded area such that the bite block can be rotated on said post relative to the backing plate.

12. The dental x-ray image media holder as in claim 11 further comprising an aiming ring adjustably secured to the holder with a support arm.

13. The dental x-ray image media holder as in claim 12 wherein said support arm is affixed to said bite block or removably affixed to said bite block.

14. The dental x-ray image media holder as in claim 13 wherein said support arm is provided with a slot for receiving said bite block, such that said bite block is frictionally retained therein.

15. A dental x-ray image media holder comprising an image media backing plate adjustably affixed to a bite block; said backing plate having at least one channel for receiving a post affixed to said bite block, such that the bite block can be selectively moved within said channel to orient the bite block in a predetermined position relative to the backing plate; wherein the backing plate is provided with a plurality of indicia, such that at least one of said indicia is used to indicate the position of the bite block relative to the backing plate, which is associated with a predetermined dental imaging procedure; and wherein said post has base such that when positioned with said channel, a portion of said backing plate is received between said base and the bite block with said post extending between and connecting said base and the bite block.

16. A dental x-ray image media holder comprising an image media backing plate adjustably affixed to a bite block; said backing plate having at least one channel for receiving a post affixed to said bite block, such that the bite block can be selectively moved within said channel to orient the bite block in a predetermined position relative to the backing plate; wherein the backing plate is provided with a plurality of indicia, such that at least one of said indicia is used to indicate the position of the bite block relative to the backing plate, which is associated with a predetermined dental imaging procedure; wherein said backing plate has a first and second sides, such that said bite block is generally positioned on said first side of said backing plate when in use; wherein said second side of said backing plate is provided with means to affix or removeably affix an image media thereto; and wherein at least one strap is secured to said backing plate, such that after an image media is placed into physical contact with said second side of said backing plate, said strap can be wrapped to physically impinge upon the image media thereby securing it in position relative to said backing plate.

17. A dental x-ray image media dental x-ray image media holder of the type having an image media backing plate affixed to a bite block and used to facilitate a dental x-ray procedure, the improvement comprising: providing a means to adjust the position of the bite block relative to the backing plate and providing a plurality of indicia to indicate the position of the bite block relative to the backing plate for a preselected dental x-ray procedure; wherein said means to adjust the position of the bite block relative to the backing plate includes providing the backing plate with at least one channel for receiving a post affixed to the bite block, such that the bite block can be selectively moved within said channel to orient the bite block in a predetermined position relative to the backing plate; and wherein the dental x-ray image media holder comprises at least two intersecting said channels and an indicia at the intersection of said at least two channels to indicate that said bite block can be rotated upon the axis of said post at said intersection.

18. The dental x-ray image media holder as in claim 17 further comprising an aiming ring adjustably secured to the holder with a support arm.

19. The dental x-ray image media holder as in claim 18 wherein said support arm is affixed to said bite block or removably affixed to said bite block.

20. The dental x-ray image media holder as in claim 19 wherein said support arm is provided with a slot for receiving said bite block, such that said bite block is frictionally retained therein.

* * * * *